United States Patent

Hessler et al.

[11] Patent Number: 6,010,243
[45] Date of Patent: Jan. 4, 2000

[54] METHOD OF ZERO-POINT SETTING OF A THERMAL CONDUCTIVITY DETECTOR SYSTEM IN A CHAMBER, ESPECIALLY FOR $CO_2$ MEASURING IN A CONTROLLED ATMOSPHERE INCUBATOR

[75] Inventors: Karlheinz Hessler; Hubert Heeg, both of Mömbris, Germany

[73] Assignee: Kendro Laboratory Products GmbH, Hanau, Germany

[21] Appl. No.: 08/907,355

[22] Filed: Aug. 7, 1997

[30] Foreign Application Priority Data

Sep. 13, 1996 [DE] Germany ............... 196 37 520

[51] Int. Cl.[7] ............ G01N 25/18; C12M 1/34; A01K 41/02
[52] U.S. Cl. ............ 374/1; 435/286.6; 436/133
[58] Field of Search ............ 374/1; 436/11, 436/133, 149, 151; 435/286.6, 303.1, 303.2, 807

[56] References Cited

U.S. PATENT DOCUMENTS

| | | | |
|---|---|---|---|
| 4,336,329 | 6/1982 | Hesse et al. | 435/3 |
| 4,701,415 | 10/1987 | Dutton et al. | 435/286.6 |
| 5,418,131 | 5/1995 | Butts | 435/5 |
| 5,635,626 | 6/1997 | Hammond et al. | 73/23.2 |

FOREIGN PATENT DOCUMENTS

| | | |
|---|---|---|
| 0 154 536 | 9/1985 | European Pat. Off. . |
| 21 33 119 | 1/1972 | Germany . |
| 33 15 085 C2 | 10/1984 | Germany . |

*Primary Examiner*—Diego Gutierrez
*Assistant Examiner*—Stanley J. Pruchnic, Jr.
*Attorney, Agent, or Firm*—Frishauf, Holtz, Goodman, Langer & Chick, P.C.

[57] ABSTRACT

A thermal conductivity detector system within an incubator having an atmosphere of moisture and $CO_2$ therein is calibrated this way: in a first phase, the incubator, after ambient air being supplied thereto, is closed with respect to further gas or air admission; in a second phase, and after a predetermined time interval, a $CO_2$ measurement is made by means of the thermal conductivity cell, and upon deviation of the measured value from a $CO_2$ zero value, the deviation is stored and utilized for 0.2 correction of the $CO_2$ measured value. A $CO_2$ tolerance range of measured values of, for example, ±0.2 vol. % $CO_2$ is determined. After introduction of moisture or humidity into the chamber, a third phase is initiated for a predetermined time interval and run through so often until the $CO_2$ measured value for the entire time interval remains within the $CO_2$ tolerance range. After successful termination of the third phase, the moisture of said value of the $CO_2$ measuring is determined, stored, and utilized for 0.2 correction of the $CO_2$ measured value. Considering the $CO_2$ offset, as well as the $CO_2$ humidity offset value, the 0.2 value of the $CO_2$ measuring is indicated, and the calibration is terminated, permitting gas valves to be opened—provided a predetermined calibration range has not been exceeded; if it has been exceeded, the calibration has to be repeated, or the range reevaluated. Thereafter, laboratory test samples can be introduced into the interior of the incubator.

10 Claims, 4 Drawing Sheets

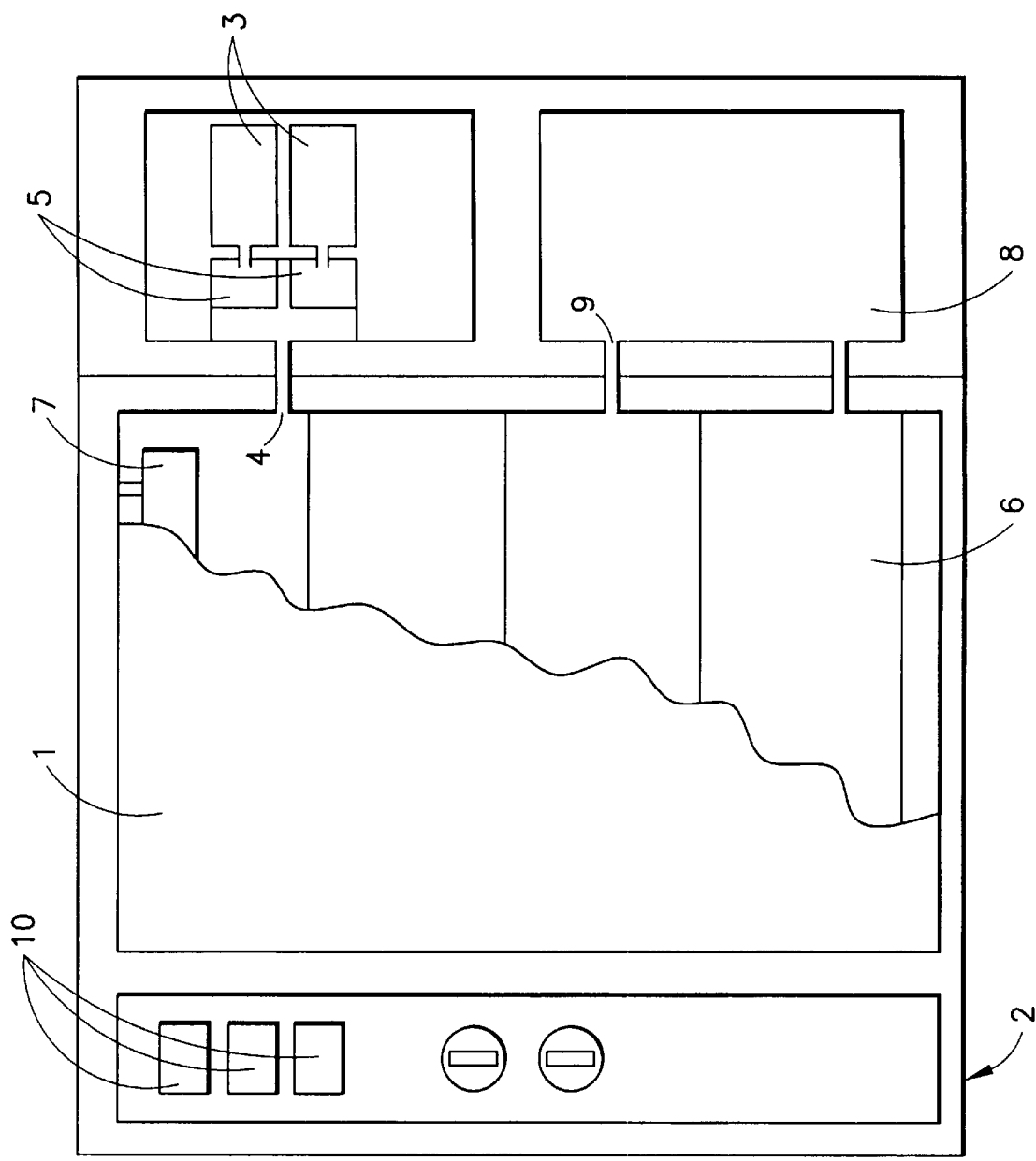

METHOD OF ZERO-POINT SETTING OF A THERMAL CONDUCTIVITY DETECTOR SYSTEM IN A CHAMBER, ESPECIALLY FOR CO₂ MEASURING IN A CONTROLLED ATMOSPHERE INCUBATOR

Reference to related patent, the disclosure of which is hereby incorporated by reference, assigned to a related company of the assignee of the present application:

U.S. Pat. No. 4,336,329, Hesse et al.

Reference to related patent literature:

German 33 15 085 C2

European 0 154 536 A3, Dutton et al.

German 21 33 119 B2, Boirat et al.

FIELD OF THE INVENTION.

The present invention relates to a method to zero-set a thermal conductivity detector system used in combination with a chamber, to control the atmosphere within the chamber, and especially a controlled atmosphere incubator. The atmosphere typically contains carbon dioxide ($CO_2$), and the thermal conductivity detector system utilizes a reference gas to regulate, or zero-set a measuring cell.

BACKGROUND

German 33 15 085 C2 describes a method for zero-setting a thermal conductivity detector (TCD) in an incubator cell, in which an atmosphere containing $CO_2$ is contained. The atmosphere can be controlled with the TCD. The measuring side, of measuring cell, or the TCD system continuously has atmosphere from the chamber applied thereto, and the measured value can be compared with a reference gas, typically ambient air.

The type of incubator chamber is known, see, for example U.S. Pat. No. 4,336,329, Hesse et al., the disclosure of which is hereby incorporated by reference.

The thermal conductivity cells have a reference side. During a measuring phase, air or some other external gas is supplied as a reference gas. During a calibrating phase, this supply is interrupted, and the reference side is exposed to the atmosphere within the chamber. The signal which is so obtained is stored, and in a measuring phase subtracted from the measuring signal desired from the measuring side of the TCD, in order to obtain a zero-offset correction signal. This correction signal is used until the next subsequent calibration phase at which time, the previously obtained correction signal is replaced by a new offset correction signal.

It has been found that this system requires a comparatively complex construction for the chamber, typically the incubator, since the reference side of the TCD must be placed in communication with the interior of the chamber, as well as with a reference gas, for example ambient external atmosphere. These communications must be absolutely separate and completely air-tight in operation. The measuring side, as well as the reference side, must never be exposed to the same atmosphere during the measuring phase. Further, the calibration is not an absolute zero-offset calibration of the entire cell, but, rather, provides a signal to correct drift of the actual sensor cells of the thermal conductivity sensor, or thermal conductivity sensor system.

German 21 33 119 B2, Boirat et al., describes an incubator having a jacket of thermal material, in which the horizontal walls of the jacket are formed of two heating plates. The upper plate is held at a controlled temperature, whereas the lower plate remains at a lower temperature. The resulting temperature gradient provides an intermediate temperature for introduced cultures of bacteria. This permits simultaneous loading of the chamber and automatic control of bacteria cultures. A plurality of controlled heating plates must be used, so that the construction is complex and expensive.

THE INVENTION.

It is an object to provide a method for automatic zero point, or zero offset determination and control, which is suitable for any type of sensor, and particularly thermal conductivity detector cell sensors or sensor systems, in which measurements are taken only in the interior of the chamber. Zero-point offset adjustment can also be carried out subsequent to a disinfection step utilizing, for example, temperatures on the order of 180° C. The method should, further, provide for stable operation within the chamber for as long a period of time as possible.

Briefly, the measuring process or method has a plurality of phases. In a first phase, the chamber, after venting, is sealed with respect to ambient atmosphere, as well as isolated from further gas supply. In a second phase, and after a lapse of a predetermined first time interval, a $CO_2$ measurement is carried out by means of a sensing cell; if the measured value from a $CO_2$ zero value differs, it is stored and utilized for zero-point correction of the $CO_2$ measured value. A $CO_2$ tolerance band of the $CO_2$ measuring value is established. Humidity is then introduced into the chamber. In a third phase, a program is run through, within a predetermined time interval, so often until the $CO_2$ measured value for the entire time interval remains within the $CO_2$ tolerance band. When the third phase is successfully finished, that is, when the $CO_2$ value is within the tolerance band, the humidity-offset value of the $CO_2$ measurement is obtained, stored, and utilized for zero-point offset correction of the $CO_2$ measured value. While taking into consideration the $CO_2$ offset value and the humidity offset value, the zero-point value of the $CO_2$ measurement is indicated and stored. If a predetermined calibration range of both offset values has not been exceeded, the zero-point offset calibration is terminated and gas valves for the desired atmosphere within the chamber can be opened. Otherwise, the entire program, or at least part of it, can be repeated.

The method has the advantage that it can be easily used with the chamber, typically an incubator. Upon placing the incubator in operation, the calibration program can be started automatically, for example after a disinfection. As soon as the program has run its course, and if appropriate offset values have not been exceeded, the incubator can be loaded with laboratory specimens and the like.

In accordance with a preferred embodiment of the invention, after a first starting step, all offset values are internally set to zero. The cell offset values can then be correctly added, algebraically, directly to $CO_2$ measured values.

A suitable $CO_2$ tolerance band for the $CO_2$ measured value, in operation, of from ±0.2 vol. % $CO_2$ has been particularly suitable.

DRAWINGS

FIG. 3a is a highly schematic view of an incubator, partly broken away, with a thermal conductivity detector system therein.

DETAILED DESCRIPTION

Figure 1:
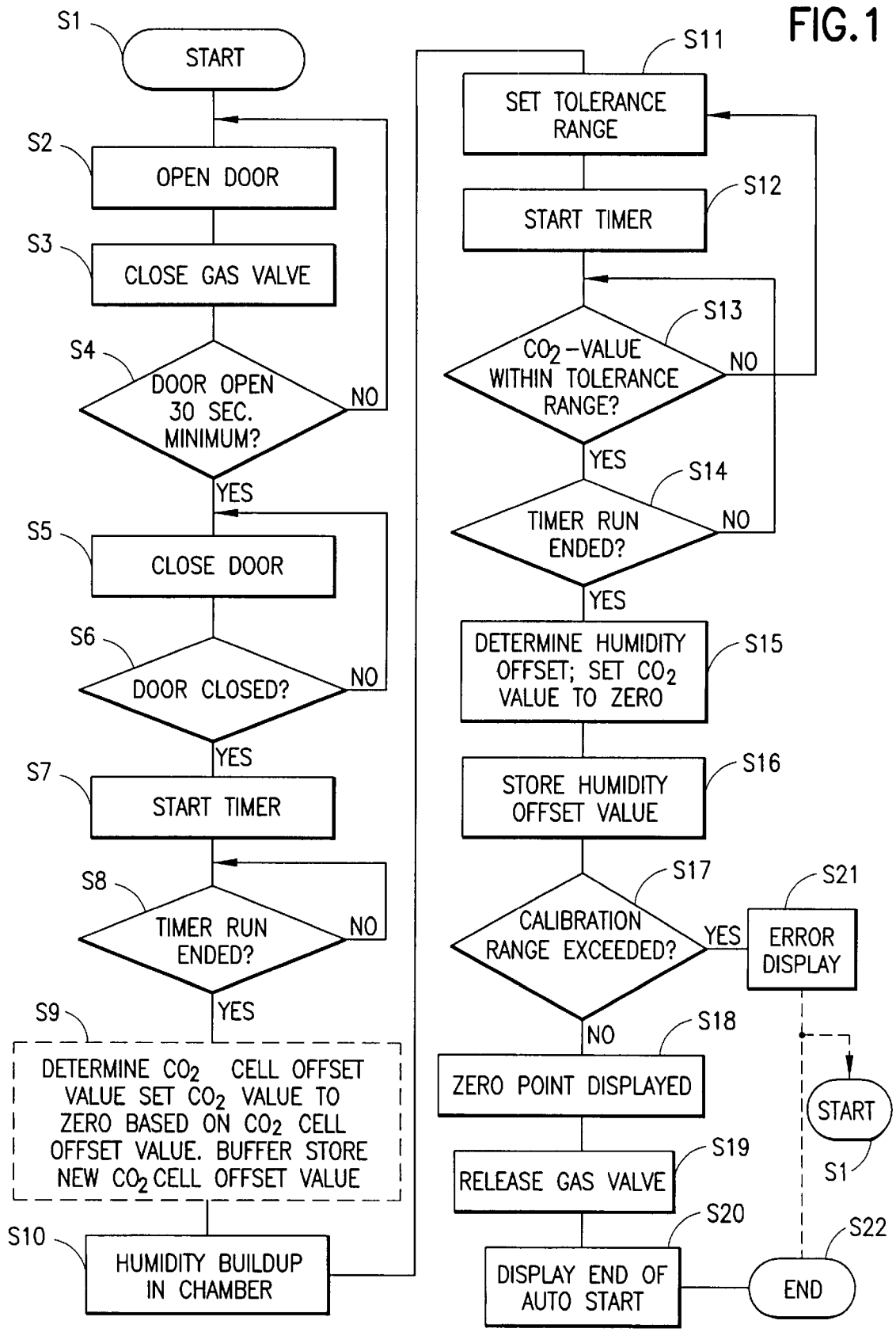
FIG. 1 is a flow diagram of the process.

Referring first to FIG. 1: The method is carried out in accordance with a program which, as is customary, starts with a start step S1. This start step can be manually initiated, or it can be initiated, for example, each time when a disinfection step of the incubator chamber has been carried out; or after an erroneous offset calibration program has run, or the calibration program was outside of a calibration range; in such case, the program can then repeat.

Step S1, the start, is followed by step S2, to open the door of the chamber, or the incubator, in order to permit atmospheric ambient air to reach the interior of the chamber. This atmosphere of ambient air forms a reference gas. Simultaneously, and parallel thereto, step S3 controls gas valves to close. The door should remain open for at least thirty seconds, and step S4 interrogates if the door has been open for thirty seconds, and if not, provides an indication that the door should be open, for example manually, and retained open.

If the minimum opening time has been met, an indication "close door" will be emitted in step S5. The closing of the door is monitored in step S6; if the door is not closed, the indication of "close door" of step S5 is repeated. When the door is closed, in step S6 the answer is YES, a first time interval is determined by starting a timer in step S7. This time interval is used to determine the $CO_2$ cell offset value. The interrogation step S8 checks if the interval has elapsed, that is, if the timer is run down after the predetermined time interval. When this time has elapsed, the $CO_2$ cell offset value is determined in step S9.

In step S9, which determines the $CO_2$ cell offset value, the $CO_2$ value is set to zero by means of the $CO_2$ cell offset value; the new $CO_2$ cell offset value is stored and a $CO_2$ tolerance band is established.

In a subsequent step S10, vapor is admitted into the chamber until a predetermined commanded humidity, for example for an incubator in the region of from between about 60 to 95% relative humidity is admitted. After the humidity has reached its value, a tolerance band, or range, is established in step S11. This tolerance range is used for subsequent determination of the humidity offset value. The timer with a second predetermined time interval is started in step S12. Step S13 determines if the $CO_2$ measured value is within the tolerance range, or not. If the answer is NO, that is, if the $CO_2$ measured value is outside of the tolerance range, the program reverts to step S11, set tolerance range. When the $CO_2$ measured value falls within the tolerance range, and the timer is run down in step S14, the $CO_2$ value is set to zero in step S15; simultaneously, in step S16, the determined humidity offset value is stored.

Thus, the $CO_2$ cell offset value as well as the $CO_2$ humidity offset value are stored.

If, upon interrogation in step S14 the timer has not yet run down, step S13 again interrogates if the $CO_2$ measured value is within the tolerance range.

In step S17, an interrogation tests if the calibration range is exceeded or not. Let it be assumed that the calibration range has not been exceeded, then, in step S18 the $CO_2$ zero-point indication is obtained and, for example, displayed, and in step S19 the gas valves for supplying the desired atmosphere within the chamber are opened. Step S20 provides a display of the automatic start, and that the starting process for zero-point determination and calibration has been successfully terminated. The program is at an end in step S22.

If, in the interrogation of step S17 the calibration range has been exceeded, step S21 provides an error display, and the program may return, for example, to a new start, that is, to step S1; it is also possible, however, to modify, or to extend, the calibration range, for example manually, at the step S22, and return, with a modified calibration range, to step S17.

Figure 2:
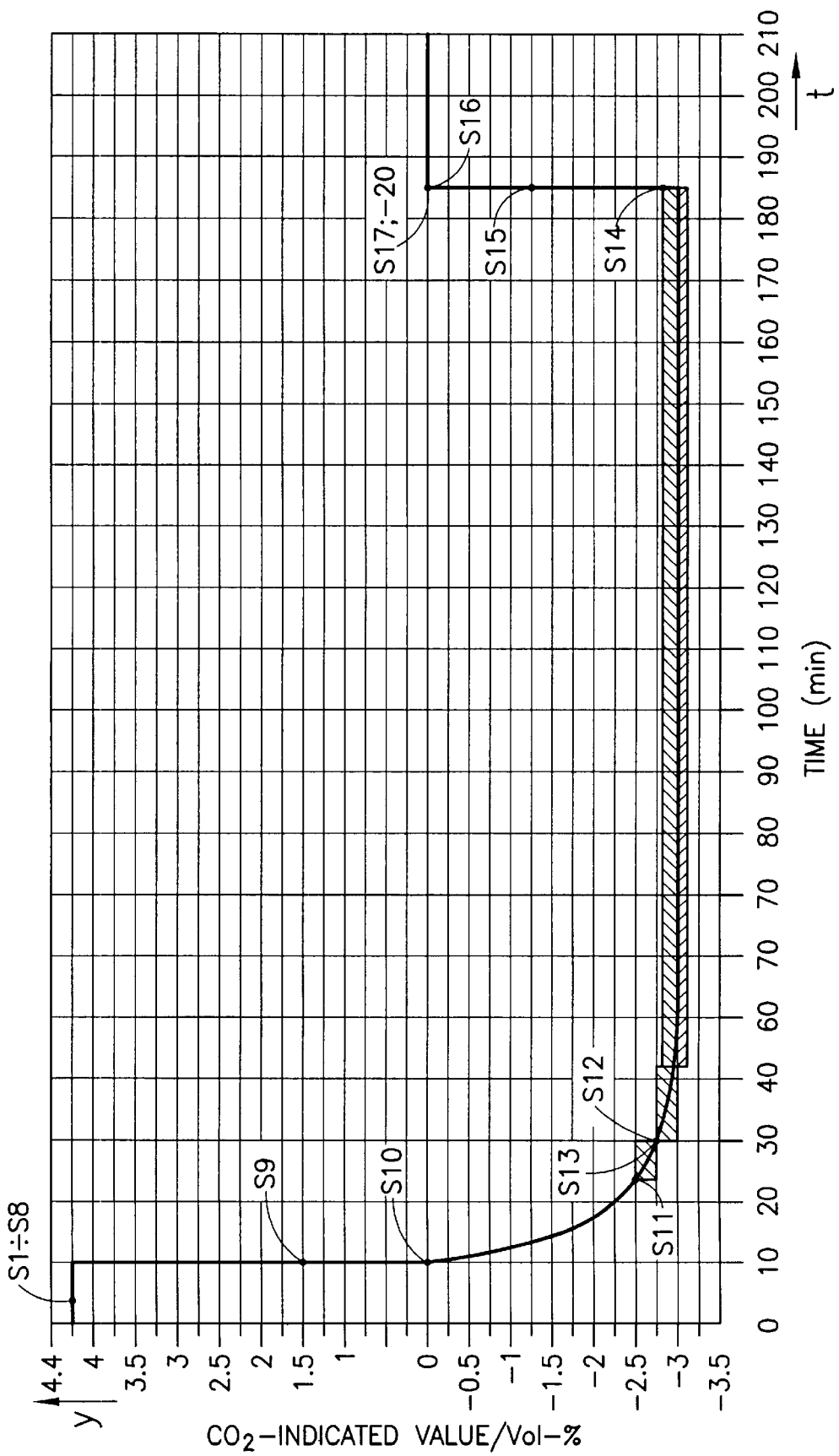
FIG. 2 is a graph of $CO_2$ indicated value with respect to time.

FIG. 2 illustrates, schematically and graphically, the automatic zero-point calibration and determination of the reference offset of a $CO_2$ thermal conductivity detector cell.

The $CO_2$ indicated value y is shown in vol. % (ordinate) with respect to a time scale, in the abscissa. The steps previously described in connection with FIG. 1 will be explained again with examples in vol. %. The subsequent explanation, thus, refers to vol. % for values y; the time t is in minutes.

At time t=0 until t=10, steps S1 through S8 are carried out, or, respectively interrogated. Let it be assumed that the timer of step S8 is run down. At the time t=10, the step S9 will then be carried out, that is, a determination made of the $CO_2$ cell offset value. The $CO_2$ value is set to zero. At time t=10, a vaporization check, and build-up of humidity in accordance with step S10 is carried out within the incubator. The increased humidity results in higher heat conductivity, and a negative $CO_2$ indicated value in a range up to 3 vol. % occurs. The humidity value and the $CO_2$ portion affect the thermal conductivity detection cell, forming the sensor, in opposite direction. In other words, an increased $CO_2$ content would result, due to heat insulation of the $CO_2$ gas within the incubator in decreased heat conductivity of the atmosphere; however, the heat conductivity increases due to the added humidity, and thus simulates a decrease of the $CO_2$ content.

Subsequent to reaching the humidity tolerance range, which is set in FIG. 1 in step S11, a suitable tolerance range is ±0.2 vol. % $CO_2$. This tolerance band, set in step S11 (FIG. 1) is, for example, after interrogation in step S13, not valid, so that the tolerance band or range must be reset, which also requires restarting the timer of step S12. After restart of the tolerance band in the region of from t=32 to t=42, a $CO_2$ measured value tolerance band in accordance with interrogation in step S13 is still not maintained, and a new start of the timer S12 will occur at time t=42; in other words, steps S11, S12 are repeated. Over the entire period from t=42 to t=185, the $CO_2$ measured value determined during the time interval of the timer S12 remains within the tolerance range. When the timer S12 has run down at time t=185 in accordance with interrogation S14, the $CO_2$ value significant for determination of the humidity offset value is set to zero in accordance with step S15. This humidity offset value is stored in step S16.

In the interrogation step S17, a check is made if the calibration range has been exceeded. If this is not the case, the preceding value of the automatic start and zero-point indicator is displayed, step S18, the gas valves are opened, S19, and the end of the zero-point calibration is indicated, step S20. Thus, after termination of the zero-point monitoring and supplying the gas to the desired value, it is possible to charge the interior of the incubator chamber with laboratory samples, which are to be exposed to an interior atmosphere with controlled $CO_2$ addition.

If, in accordance with the interrogation step S17, the calibration range has been exceeded, an error indication is obtained in step S21. The program can then revert to the time t=0 for a new start, if necessary and desired.

The construction of an incubator chamber is known by itself. FIG. 3a illustrates, highly schematically, the construction of such a known incubator chamber in which the zero-point calibration of a thermal conductivity cell system is carried out. The construction, itself, is also described in U.S. Pat. No. 4,336,329, Hesse et al., the disclosure of which is hereby incorporated by reference, as well as in German 33 15 085 C2. Further discussion relating to gas flow and control of temperature, gas admission, humidity and the like, thus, is not necessary here, since the prior art in connection therewith is well known.

The door 1 (FIG. 3a) of the incubator 2 is opened at the beginning of the program. Gas valves 5, controlling gas admission, of for example, gas supplies 3 and gas venting, for example, valves 4, are closed. After a minimum opening time of about 30 seconds (step S4), the door is closed. The gas supply 3, for example, is coupled to a source of $CO_2$ under pressure. Other supplies can be coupled, for example pure oxygen, or pure nitrogen. Additional filters and pre-heaters can be located between the valves 5 and the entry of gases into the interior 6 of the incubator 2. Such filters and preheaters have been omitted from the drawings for clarity.

Figure 3B:
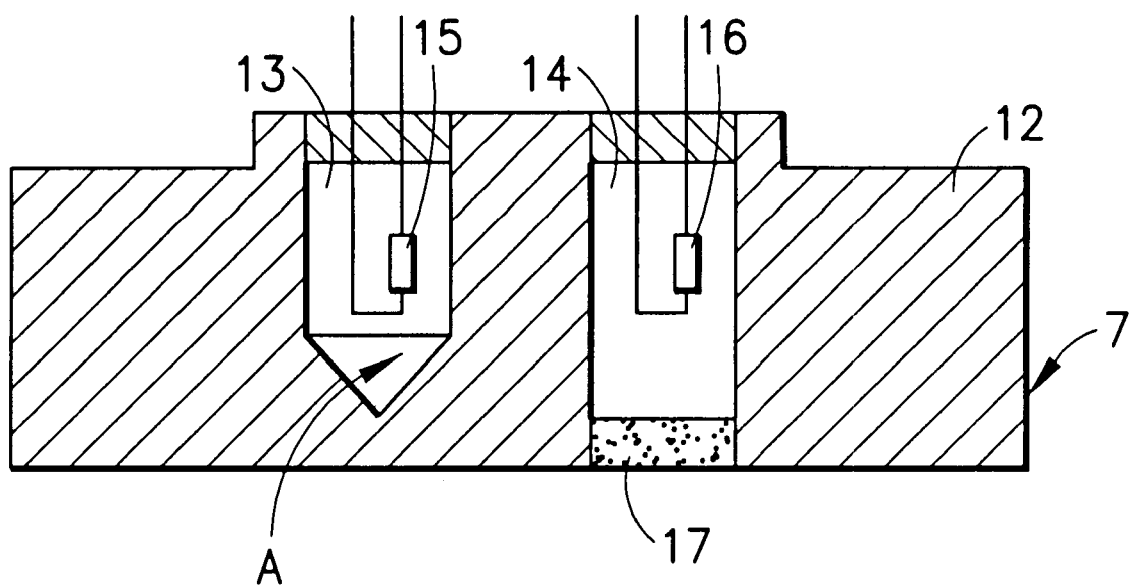
FIG. 3b is a schematic cross-sectional view through the cells of a thermal conductivity detector system.

The upper region of the chamber 6, that is the interior space of the incubator 2, illustrates, highly schematically, the placement of the thermal conductivity detector system 7, which is shown in detail in FIG. 3b. A vapor supply unit 8 is coupled over a line 9 with the chamber 6, that is, the interior of the incubator 2. Thus, besides temperature control, control of the relative humidity to provide an electronically controlled inner atmosphere within the incubator is provided for. Gas supply, as well as the vaporization system, together with measuring and control instrumentation, is well known from the above-referenced U.S. Pat. No. 4,336,329, as well as from commercially available apparatus, described, for example in the patent literature in German 33 18 085 C2. A detailed description of these well-known, and commercially used systems, thus, is not here necessary.

The measuring cell 7 is shown in FIG. 3b highly schematically, in cross-section. A metallic block 12 is maintained at a predetermined temperature level, for example 37° C. by thermostatic control, as is well known. The metallic block 12 is formed with two relatively spaced bores 13, 14, each of which retain a negative temperature coefficient (NTC) resistor 15, 16, respectively. Bore 13 forms a reference bore and is gas-tightly closed with respect to the ambient surroundings. Bore 14 is used as a measuring bore, and coupled through a filter 17 to form a gas connection with the chamber 6 of the incubator 2, in accordance with FIG. 3a. The NTC resistors 15, 16 can be operated at a substantially higher temperature level than the temperature of the metal block 12. Thus, heat flow passes, in heat conduction direction, towards the metal block 12. The NTC reference resistor 15, in the reference bore 13, provides for a constant heat flow from the NTC resistor 15 to the block 12, which forms an isothermal heat sink. The heat flow from the bore 14, however, is additionally influenced by the atmosphere passing through the filter 17. Possible variations in temperature at the measuring side can be so controlled by means of the uniformly maintained thermal conditions that temperature variations through the reference side can be compensated.

For comparison of the reference side and measuring side, a customary servo control is used, well known from the prior art, for example as discussed in the introduction to the present specification. The reference gas, preferably, is air which is supplied in form of an air stream; U.S. Pat. No. 4,336,329, Hesse et al., is here referred to. The air stream is schematically shown by arrow A, FIG. 3b.

We claim:

1. A method of zero-point adjustment of a thermal conductivity detector cell sensor system having thermal conductivity detector cells, including a measuring cell, connected to control the atmosphere within a chamber, in which the atmosphere contains $CO_2$, comprising the steps of
in a first phase:
 (a) opening the chamber to ambient atmosphere;
 (b) closing the chamber and isolating the chamber with respect to ambient atmosphere and any other external gas sources;
in a second phase:
 (c) establishing a first timing interval;
 (d) establishing a $CO_2$ tolerance band within a predetermined tolerance range for measured $CO_2$ % concentration values;
 (e-1) at the expiration of said first timing interval, carrying out a measurement of $CO_2$ by said measuring cell, and
 (e-2) if a deviation from zero is detected, resetting the $CO_2$ value to zero, repeating steps (c) through (e-1) until the $CO_2$ value is within the tolerance band, and storing said deviation, within the tolerance band, to obtain a $CO_2$ zero-point correction offset value;
 (f) introducing water vapor into said chamber;
in a third phase:
 (g-1) establishing a second timing interval;
 (g-2) at the expiration of said second timing interval, carrying out a measurement of $CO_2$ by said measuring cell, and
 (h) if a deviation from zero is detected, resetting the $CO_2$ value to zero, repeating steps (g-1) and (g-2) until the measured $CO_2$ value remains within said tolerance band during at least a major portion of said second timing interval, to thereby obtain a humidity-$CO_2$ offset value;
 (i) utilizing said humidity-$CO_2$ zero-point offset value to modify, if necessary, the $CO_2$ zero-point correction offset value;
 (j) determining a calibration limit range;
 (k-1) if the calibration limit range has not been exceeded, indicating the zero-point offset value of the $CO_2$ measurement, based on the $CO_2$ offset value and the humidity-$CO_2$ value, terminating the zero-point adjustment procedure and admitting gas into the chamber;
 (k-2) if the calibration limit range has been exceeded, providing an error display and, optionally, resetting the calibration range limit of step (j) and then repeating steps (a) through (k-1) or (k-2).

2. The method of claim 1, further comprising the step of resetting all offset values of the thermal conductivity detector system internally to zero before, or immediately after, a starting step in advance of step (a).

3. The method of claim 2, further comprising the step of adding determined thermal conductivity sensor offset values to the measured $CO_2$ offset values.

4. The method of claim 1, wherein said second timing interval established in step (g-1) is long enough to result in an equilibrium state of water vapor introduced in step (f);

wherein the humidity-$CO_2$ offset value determined in step (h) is tested over at least a major portion of said second timing interval for maintenance within the $CO_2$ tolerance band established in step (d);

and wherein said tolerance band is in the region of about ±0.2 vol. % $CO_2$.

5. The method of claim 4, wherein the determined $CO_2$ value within the tolerance band determined in step (d) is stored and added to a new zero-point offset correction of the $CO_2$ thermal conductivity sensor.

6. The method of claim 4, wherein, if the $CO_2$ measured value exceeds or falls below a predetermined $CO_2$ measured value, the step is carried out of terminating the zero-point adjustment method and providing an error indication.

7. The method of claim 6, including the step of restarting the method subsequent to a start step which includes the step of resetting all offset values of the thermal conductivity sensors to zero.

8. The method of claim 1, wherein said thermal conductivity detector cells comprises a first thermal conductivity sensor cell exposed to the atmosphere within the chamber and a second thermal conductivity sensor cell exposed to a reference gas.

9. The method of claim 8, wherein said reference gas comprises air.

10. The method of claim 9, wherein said reference gas comprises air in the form of an air stream.

* * * * *